US012806593B2

(12) United States Patent

Tachikawa et al.

(10) Patent No.: US 12,806,593 B2
(45) Date of Patent: Nov. 24, 2026

(54) PREDICTION DEVICE, CALCULATION DEVICE, MANUFACTURING DEVICE, AND MANUFACTURING METHOD

(71) Applicant: DAIKIN INDUSTRIES, LTD., Osaka (JP)

(72) Inventors: Shouhei Tachikawa, Osaka (JP); Takaya Yamada, Osaka (JP); Fumiko Shigenai, Osaka (JP); Rumi Kawabe, Osaka (JP); Shingo Morita, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 758 days.

(21) Appl. No.: 18/084,637

(22) Filed: Dec. 20, 2022

(65) Prior Publication Data

US 2023/0119336 A1 Apr. 20, 2023

Related U.S. Application Data

(63) Continuation of application No. PCT/JP2021/025156, filed on Jul. 2, 2021.

(30) Foreign Application Priority Data

Jul. 3, 2020 (JP) ................................. 2020-115514

(51) Int. Cl.
*B01J 19/00* (2006.01)
*B01J 19/06* (2006.01)
(Continued)

(52) U.S. Cl.
CPC ........... *B01J 19/0033* (2013.01); *B01J 19/06* (2013.01); *C08F 14/18* (2013.01); *G01N 33/445* (2013.01); *B01J 2219/00243* (2013.01)

(58) Field of Classification Search
CPC ...... G16C 60/00; G16C 20/30; G01N 33/445; B01J 19/0033; C08F 2/01; C08F 2400/02
See application file for complete search history.

(56) References Cited

U.S. PATENT DOCUMENTS

| | | | |
|---|---|---|---|
| 2021/0162362 | A1 | 6/2021 | Inaba et al. |
| 2021/0162363 | A1 | 6/2021 | Inaba et al. |

FOREIGN PATENT DOCUMENTS

| | | | |
|---|---|---|---|
| CN | 101650290 | A | 2/2010 |
| JP | 04-320405 | A | 11/1992 |

(Continued)

OTHER PUBLICATIONS

Extended European Search Report dated Dec. 9, 2024 from the European Patent Office in Application No. 21833888.7.

(Continued)

*Primary Examiner* — Mark S Kaucher
(74) *Attorney, Agent, or Firm* — Sughrue Mion, PLLC

(57) ABSTRACT

A variation in the performance value of a polymer being manufactured can be reduced. A prediction device (10A) that, in manufacturing of a polymer, predicts a performance value indicating performance of the polymer in a polymerization tank after a raw material is fed, and may include: an acquisition unit (111) that acquires, as a prediction observation value, an observation value observed, in current manufacturing of the polymer, as a value related to the manufacturing of the polymer; and a prediction unit (112) that predicts the performance value of the polymer being currently manufactured at a predetermined timing, from the prediction observation value acquired by the acquisition unit, by using a relation between an observation value acquired in past manufacturing of the same type of polymer as the polymer, and a performance value of the polymer at the predetermined timing in the past manufacturing.

3 Claims, 11 Drawing Sheets

(51) Int. Cl.
*C08F 14/18* (2006.01)
*G01N 33/44* (2006.01)

(56) References Cited

FOREIGN PATENT DOCUMENTS

| | | | |
|---|---|---|---|
| JP | 05-140230 | A | 6/1993 |
| JP | 2001-294603 | A | 10/2001 |
| JP | 2003-076934 | A | 3/2003 |
| JP | 2007-191657 | A | 8/2007 |
| JP | 2011-525967 | A | 9/2011 |
| JP | 2011-245742 | A | 12/2011 |
| JP | 2015-520674 | A | 7/2015 |
| JP | 2018-162410 | A | 10/2018 |
| JP | 2019-178256 | A | 10/2019 |
| JP | 2020-038495 | A | 3/2020 |
| WO | 03/006955 | A1 | 1/2003 |
| WO | 2009/149328 | A2 | 12/2009 |
| WO | 2013/175240 | A1 | 11/2013 |
| WO | 2020/054183 | A1 | 3/2020 |
| WO | 2020/066309 | A1 | 4/2020 |

OTHER PUBLICATIONS

Huaiping Jin et al., “Ensemble Just-In-Time Learning-Based Soft Sensor for Mooney Viscosity Prediction in an Industrial Rubber Mixing Process”, Advances in Polymer Technology, 2020, vol. 2020, pp. 1-14 (14 pages total).

Shuihua Zheng et al., “Robust Soft Sensor with Deep Kernel Learning for Quality Prediction in Rubber Mixing Processes”, Sensors, 2020, vol. 20, No. 3, pp. 695 (10 pages total).

Kai Yang et al., “Soft sensor development for online quality prediction of industrial batch rubber mixing process using ensemble just-in-time Gaussian process regression models”, Chemometrics and Intelligent Laboratory Systems, 2016, vol. 155, pp. 170-182 (13 pages total).

Nagasawa, “Structure and physical property of ethylene propylene rubbers”, Journal of the Society of Rubber Science and Technology, vol. 51, No. 9, pp. 677-684, 1978 (9 pages total).

Ono, “Industrial Synthetic Method of the Rubbers, 9. Polyolefin Elastomers”, Journal of the Society of Rubber Science and Technology, vol. 89, No. 3, pp. 63-67, 2016 (6 pages total).

International Preliminary Report on Patentability with the translation of Written Opinion dated Dec. 13, 2022 from the International Bureau in International Application No. PCT/JP2021/025156.

Out of Time Validation, A data division/evaluation method for machine learning models (online), Jan. 4, 2020 (Searching Date: Apr. 17, 2023), Internet: <URL:http://starpentagon.net/analytics/detaset_split_evaluation/>.

International Search Report of PCT/JP2021/025156 dated Sep. 21, 2021 [PCT/ISA/210].

PREDICTION DEVICE, CALCULATION DEVICE, MANUFACTURING DEVICE, AND MANUFACTURING METHOD

This application is a Rule 53(b) Continuation of International Application No. PCT/JP2021/025156 filed Jul. 2, 2021, which claims priority from Japanese Patent Application No. 2020-115514 filed Jul. 3, 2020, the respective disclosures of which are incorporated herein by reference in their entirety.

The present disclosure relates to a prediction device, a calculation device, a manufacturing device, and a manufacturing method that are used in manufacturing of a polymer.

BACKGROUND ART

Conventionally, soft sensors are used in various fields. A soft sensor estimates a quantity by using a process variable that is relatively easy to measure, such as temperature or pressure, in place of a process variable y1 that is difficult to measure and is not frequently measured, or a process variable y2 that needs time to be measured. For example, JP 2011-245742 A discloses a system for pelletizing polyolefin resin, including a soft sensor that estimates a melt flow rate.

SUMMARY

The present disclosure provides a prediction device, a calculation device, a manufacturing device, and a manufacturing method that can reduce the number of steps required in a manufacturing process for acquiring a polymer with a specific performance value.

A prediction device of the present disclosure may be a prediction device that, in manufacturing of a polymer, predicts a performance value indicating performance of the polymer in a polymerization tank after a raw material is fed, and may include: an acquisition unit that acquires, as a prediction observation value, an observation value observed, in current manufacturing of the polymer, as a value related to the manufacturing of the polymer; and a prediction unit that predicts the performance value of the polymer being currently manufactured at a predetermined timing, from the prediction observation value acquired by the acquisition unit, by using a relation between an observation value acquired in past manufacturing of the same type of polymer as the polymer, and a performance value of the polymer at the predetermined timing in the past manufacturing.

In the prediction device, the prediction unit may predict the performance value of the polymer being currently manufactured at the predetermined timing, from the prediction observation value acquired by the acquisition unit, by using a trained model that has learned, through machine learning, a relation between a training observation value acquired in past manufacturing of the same type of polymer as the polymer, and a performance value of the polymer at the predetermined timing in the past manufacturing.

In the prediction device, the acquisition unit may acquire the observation value along with elapsed time since start of the current manufacturing, and uses a set of the elapsed time and the observation value for the prediction observation value, and the prediction unit may predict the performance value of the polymer being currently manufactured at the predetermined timing, by using a relation between a training observation value that is a set of the observation value in the past manufacturing and elapsed time since start of the past manufacturing, and the performance value at the predetermined timing in the past manufacturing.

In the prediction device, the prediction unit may predict the performance value of the polymer at the predetermined timing, by using the trained model that is trained by using at least one observation value or performance value suitable for prediction of the performance value, the at least one observation value or performance value being selected, based on a genetic algorithm, from a plurality of types of observation values acquired in the past manufacturing and performance values of the polymer acquired in the past manufacturing.

In the prediction device, the observation value may include at least any of a stirring electric current value of a stirrer that stirs a reaction mixture including the raw material in the polymerization tank, a stirring electric power value, a pressure value in the polymerization tank, an amount of any of raw materials fed from start of manufacturing until a current time point, and an amount of all raw materials fed from start of manufacturing until a current time point.

In the prediction device, the performance value may be any of a Mooney viscosity, an average molecular weight, a specific gravity, a hardness, an elongation, a minimum torque, a maximum torque, an induction time to start of curing, an optimal curing time, a tensile strength, a 100% tensile stress, a glass-transition temperature, an initial pyrolysis temperature, and a compression set rate.

In the prediction device, the polymer may be an elastomer.

In the prediction device, the predetermined timing may be a timing at which a fed amount of a predetermined raw material of the polymer being manufactured becomes a predetermined value, or a timing at which a predetermined time period passes after start of manufacturing.

A calculation device of the present disclosure may be a calculation device that, in manufacturing of a polymer, obtains a target timing at which a specific operation is performed for terminating the manufacturing of the polymer in a polymerization tank, and may include: a receiving unit that receives a target performance value indicating a target of performance of the polymer in current manufacturing, and a performance value at a predetermined timing after a raw material of the polymer is fed and before the manufacturing is terminated; and a calculation unit that obtains the target timing at which the polymer being currently manufactured achieves the target performance value, by using a relation among a performance value of the polymer at the predetermined timing in past manufacturing of the same type of polymer as the polymer, a performance value of the polymer acquired in the past manufacturing, and a target timing in the past manufacturing, and by using the target performance value and the performance value at the predetermined timing received by the receiving unit.

In the calculation device, the calculation unit may obtain the target timing at which the polymer being currently manufactured achieves the target performance value, by using a second trained model that has learned, through machine learning, the relation among the performance value of the polymer at the predetermined timing in the past manufacturing of the same type of polymer as the polymer, the performance value of the polymer acquired in the past manufacturing, and the target timing in the past manufacturing, and by using the target performance value and the performance value at the predetermined timing.

In the calculation device, the calculation device may be connected to the prediction device as described above, and the receiving unit may receive, as the performance value at the predetermined timing, the performance value predicted by the prediction device.

Another calculation device of the present disclosure may be a calculation device that, in manufacturing of a polymer, obtains a target timing used to determine termination of the manufacturing of the polymer, and may include: a receiving unit that receives, as a calculation observation value, an observation value observed, in current manufacturing, as a value related to the manufacturing of the polymer, and receives, as a target value, a target performance value indicating a target of performance of the polymer in the current manufacturing; and a calculation unit that obtains a target timing in the current manufacturing, from the calculation observation value received by the receiving unit, by using a relation among an observation value acquired in past manufacturing of the same type of polymer as the polymer, a performance value of the polymer acquired in the past manufacturing, and a target timing in the past manufacturing.

In the calculation device, the calculation unit may obtain the target timing, from the calculation observation value, by using a third trained model that has learned, through machine learning, a relation among a training observation value acquired in past manufacturing of the same type of polymer as the polymer, a performance value of the polymer acquired in the past manufacturing, and a target timing in the past manufacturing.

In the calculation device, the polymer may be an elastomer.

A manufacturing device of the present disclosure may include: a polymerization tank into which a raw material of a polymer is fed; an acquisition unit that acquires, as a prediction observation value, an observation value observed, in current manufacturing of the polymer, as a value related to the manufacturing of the polymer; a prediction unit that predicts a performance value of the polymer being currently manufactured at a predetermined timing, from the prediction observation value acquired by the acquisition unit, by using a relation between an observation value acquired in past manufacturing of the same type of polymer as the polymer, and a performance value of the polymer at the predetermined timing in the past manufacturing; a receiving unit that receives a target performance value indicating a target of performance of the polymer in the current manufacturing, and the performance value at the predetermined timing predicted by the prediction unit; a calculation unit that obtains a target timing at which the polymer being currently manufactured achieves the target performance value, by using a relation among the performance value of the polymer at the predetermined timing in the past manufacturing of the same type of polymer as the polymer, a performance value of the polymer acquired in the past manufacturing, and a target timing in the past manufacturing, and by using the target performance value and the performance value at the predetermined timing received by the receiving unit; and a control unit that terminates the current manufacturing, by using the target timing obtained by the calculation unit.

A manufacturing method of the present disclosure may include: feeding a raw material of a polymer into a polymerization tank; acquiring, as a prediction observation value, an observation value observed, in current manufacturing of the polymer, as a value related to the manufacturing of the polymer; predicting a performance value of the polymer being currently manufactured at a predetermined timing, from the acquired prediction observation value, by using a relation between an observation value acquired in past manufacturing of the same type of polymer as the polymer, and a performance value of the polymer at the predetermined timing in the past manufacturing; receiving a target performance value indicating a target of performance of the polymer in the current manufacturing, and the predicted performance value at the predetermined timing; obtaining a target timing at which the polymer being currently manufactured achieves the target performance value, by using a relation among the performance value of the polymer at the predetermined timing in the past manufacturing of the same type of polymer as the polymer, a performance value of the polymer acquired in the past manufacturing, and a target timing in the past manufacturing, and by using the received target performance value and the received performance value at the predetermined timing; and terminating the current manufacturing, by using the obtained target timing.

Generalized specific embodiments of the foregoing may be implemented by any one of a system, a method, and a computer program, or a combination thereof.

According to the prediction device, the calculation device, the manufacturing device, and the manufacturing method of the present disclosure, the number of steps required in the process of manufacturing a polymer can be reduced.

DESCRIPTION OF EMBODIMENTS

Figure 1:
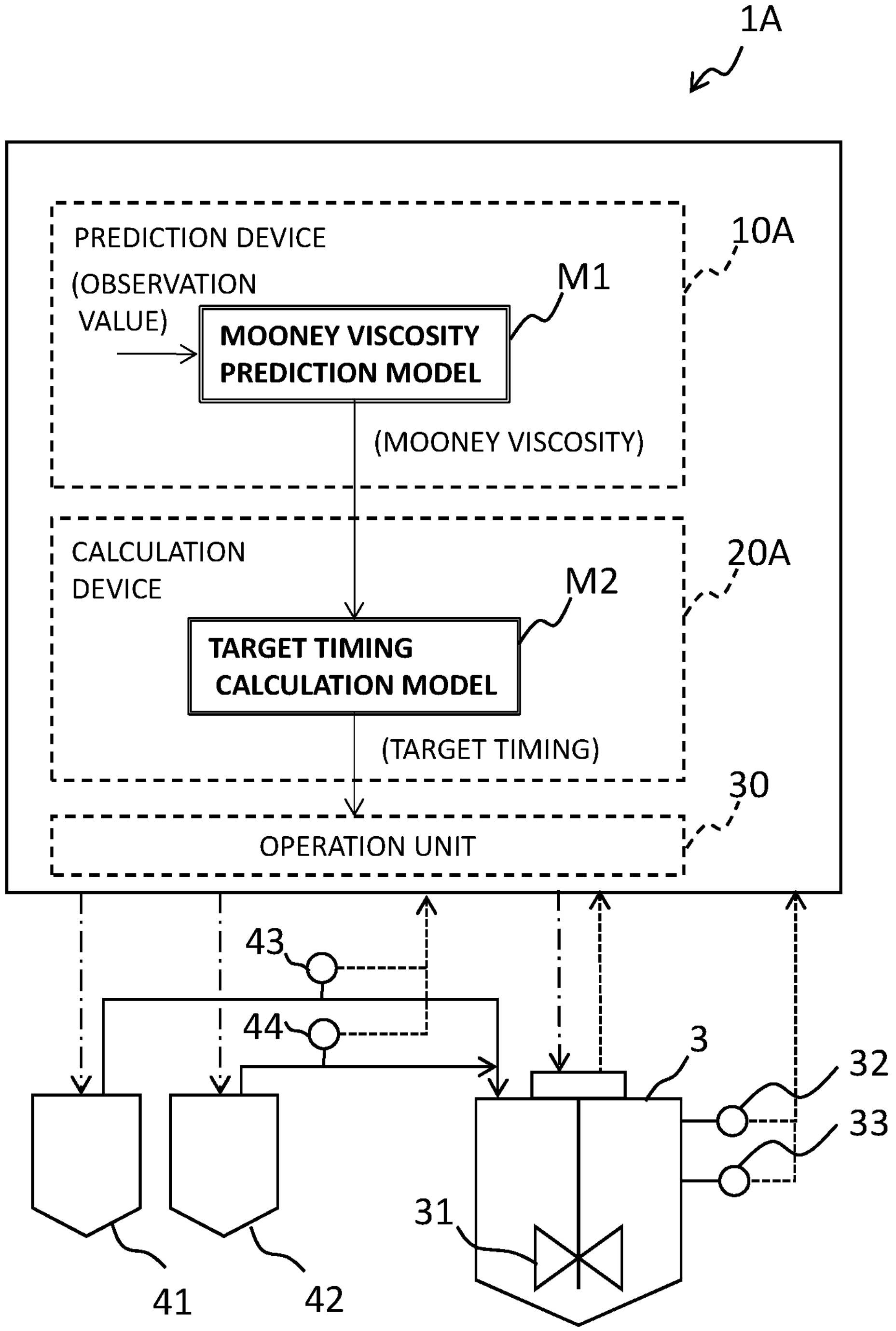
FIG. 1 is a schematic diagram showing a configuration of a manufacturing device in an embodiment 1.

An example of a method for manufacturing a polymer is that raw materials of a polymer to be manufactured are fed into a polymerization tank, and the polymer is acquired by polymerization reaction in the polymerization tank. In such cases, feeding of the raw materials into the polymerization tank is performed not only by feeding all raw materials at a time, but a raw material is fed halfway through manufacturing in some cases. For example, among the raw materials, which include a monomer and an initiator, some can be fed initially, some can be fed intermittently, some can be fed continuously, and so forth. There are also some cases where different methods are used in combination respectively for a plurality of types of raw materials that are used to generate a polymer. Specifically, when a polymer is manufactured by using a raw material A and a raw material B, the raw material A may be fed only initially, while the raw material B may be fed intermittently.

Such manufacturing of a polymer is not always finished after the same manufacturing time period, and requires 50 hours on one occasion, requires 70 yours on another occasion, and so forth even if the same polymer is manufactured, so that each process step in manufacturing cannot be determined only depending on time. For example, a manufacturing process advances to a next step when the fed amount of a specific raw material reaches a predetermined amount, in some cases. Moreover, for example, the process advances to a next step on condition that the performance of a polymer in the course of manufacturing reaches a predetermined value, in some cases. For example, the case where the process advances to a next step depending on the fed amount of a raw material can be relatively easily implemented by observing the fed amount of the raw material. On the other hand, when the process advances to a next step depending on a predetermined value related to the performance of a polymer in the course of manufacturing, it is difficult to observe in real time the performance value of the polymer in the course of manufacturing. Accordingly, it is difficult to track each situation in manufacturing of a polymer, so that the polymer being manufactured tends to vary in performance.

To observe the performance value of a polymer being manufactured, it is necessary to sample, from a polymerization tank, and perform measurement for the polymer being manufactured. However, an operation of sampling the polymer from the polymerization tank requires no small amount of operation time.

Incidentally, in manufacturing of a polymer, many types of materials are used, and many types of equipment are used. Moreover, a long time is required for manufacturing. Accordingly, there are many candidates for data that can be used by a soft sensor. It is therefore indeterminate which data is preferred when used by the soft sensor, so that it is also difficult to easily use the soft sensor.

A prediction device, a calculation device, a manufacturing device, and a manufacturing method according to each embodiment, which will be described below with reference to the drawings, reduce the number of steps required in a manufacturing process. The "prediction device" of the present disclosure predicts, in manufacturing of a polymer, a "performance value" that specifies performance of the polymer at a predetermined timing, by using an observation value acquired as a value related to the manufacturing. By using the prediction device, a performance value can be predicted in manufacturing of a polymer, without actually sampling, from a polymerization tank, and measuring the polymer. Accordingly, for example, a degree of progress of polymerization in manufacturing of a polymer can be found, without actually measuring the polymer.

The "calculation device" obtains, in manufacturing of a polymer, a "target timing" that is used to determine termination of the manufacturing of the polymer, by using a performance value of the polymer at a predetermined timing, or an observation value acquired in the manufacturing. By using the calculation device, a target timing can be determined in manufacturing of a polymer, without actually sampling the polymer from a polymerization tank and measuring performance of the polymer.

The "manufacturing method" and the "manufacturing device" manufacture a polymer by using a predicted performance value and an obtained target timing. In a description below, the same components are denoted by the same signs, and a description thereof is omitted.

A "polymer" being manufactured by the manufacturing device is a polymer that is a compound obtained as a result of polymerization of one or more types of monomers. In the following description, the "polymer" is assumed to be, but is not limited to, an "elastomer". For example, the "elastomer" is a "fluoroelastomer", a "non-fluoroelastomer", or the like.

In one embodiment, the polymer is a fluoroelastomer, and more particularly a perfluoroelastomer.

The glass-transition temperature of the fluoroelastomer may be 25° C. or less, preferably 0° C. or less, more preferably −5° C. or less, even more preferably −10° C. or less, or may be −20° C. or less. Here, the glass-transition temperature is acquired as follows. A DSC curve is acquired by using a differential scanning calorimeter (X-DSC 823e, manufactured by Hitachi Technoscience Corporation), by lowering the temperature to −75° C. and then raising the temperature at 20° C./minute, and a temperature corresponding to a point where an extended line from a base line of the DSC curve around a second-order transition intersects with a tangent line to the DSC curve at an inflection point is used for the glass-transition temperature.

The fluoroelastomer may be, for example, an elastomer including a structural unit derived from at least one monomer selected from the group consisting of tetrafluoroethylene (TFE), vinylidene fluoride (VdF), and perfluoroethylene unsaturated compounds (for example, hexafluoropropylene (HFP), perfluoro(alkyl vinyl ether) (PAVE), and the like) represented by a following formula (1):

$$CF_2{=}CF{-}R_f^a \quad (1)$$

where $R_f^a$ is $-CF_3$ or $-OR_f^b$, where $R_f^b$ is a perfluoroalkyl group with one to five carbons.

The fluoroelastomer may be perfluoroelastomer including tetrafluoroethylene (TFE) such as tetrafluoroethylene (TFE)/perfluoroalkyl vinyl ether fluoroelastomer, vinylidene fluoride (VdF) fluoroelastomer, TFE/propylene (Pr) fluoroelastomer, TFE/Pr/VdF fluoroelastomer, ethylene (Et)/hexafluoropropylene (HFP) fluoroelastomer, Et/HFP/VdF fluoroelastomer, Et/HFP/TFE fluoroelastomer, fluorosilicone fluoroelastomer, fluorophosphazene fluoroelastomer, or the like.

The perfluoroelastomer may be formed of TFE/PAVE or the like. The composition of TFE/PAVE is preferably (50 to 90)/(50 to 10) (mol %), more preferably (50 to 80)/(50 to 20) (mol %), even more preferably (55 to 75)/(45 to 25) (mol %).

PAVE in such a case may be, for example, perfluoromethyl vinyl ether (PMVE), perfluoropropyl vinyl ether (PPVE), or the like, which can be used in isolation, or in arbitrary combination.

The percentage of fluorine in the fluoroelastomer is preferably 50 mass % or more, more preferably 55 mass % or more, even more preferably 60 mass % or more. The upper limit of the percentage of fluorine content is not limited, and is preferably 71 mass %.

The above-mentioned examples of the fluoroelastomer are compositions of a main monomer, and those copolymerized with a monomer giving a crosslinkable group can also be used suitably. The monomer giving a crosslinkable group may be any monomer that can introduce an appropriate crosslinkable group, according to a manufacturing method or a crosslink system, and may be, for example, a known polymerizable compound including an iodine atom, a bromine atom, a carbon-carbon double bond, a cyano group, a carboxyl group, a hydroxyl group, an amino group, an ester group, or the like, or may be a chain transfer agent or the like.

The non-fluoroelastomer may be diene rubber, such as acrylonitrile-butadiene rubber (NBR) or hydride thereof (HNBR), styrene-butadiene rubber (SBR), chloroprene rubber (CR), butadiene rubber (BR), natural rubber (NR), or isoprene rubber (IR), or may be ethylene-propylene-termonomer copolymer rubber, silicone rubber, butyl rubber, epichlorohydrin rubber, acrylic rubber, chlorinated polyethylene (CPE), polymer alloy of acrylonitrile-butadiene rubber and vinyl chloride (PVC-NBR), ethylene-propylene-diene monomer (EPDM) rubber, or the like.

In the following description, a "performance value" is assumed to be, but is not limited to, a "Mooney viscosity" of an elastomer. Specifically, the performance value may be any value that indicates performance of a polymer. For example, the "performance value" is any of "average molecular weight", "specific gravity relative to 4° C. water as a reference (hereinafter, simply referred to as "specific gravity")", "hardness", "elongation", "minimum torque", "maximum torque", "induction time to start of curing", "optimal curing time", "tensile strength", "100% tensile stress", "glass-transition temperature", "initial pyrolysis temperature", and "compression set rate" of a polymer being manufactured. The performance value may be a value obtained based on a function by using a plurality of ones selected from among the above-mentioned performance values.

A "target timing" is a timing at which a specific operation for terminating manufacturing is performed, and is assumed here to be a "timing at which a specific operation is performed to achieve a target performance value of an elastomer when manufacturing is terminated". The specific operation for terminating manufacturing is, for example, stopping feeding a raw material, stopping stirring, reducing pressure in the tank, starting cooling, or the like. The "target timing" needs to be obtained according to a situation. For example, the "target timing" can be obtained according to an observation value observed as a value related to manufacturing of a polymer. "Start" of manufacturing is determined, for example, by a first timing of feeing a raw material. "Termination" of manufacturing corresponds to a timing at which, after the target timing is reached, a manufactured polymer becomes able to be extracted or transported due to a predetermined condition for termination being met. The "condition for termination" is that, for example, polymerization substantially ceases, the inside of the polymerization tank becomes a predetermined temperature, the inside of the polymerization tank becomes a predetermined pressure value, a predetermined time period passes after last feeding, or the like.

In manufacturing of an elastomer, an "observation value" is a value observed, in manufacturing of a polymer, as a value related to the manufacturing of the polymer, and is, for example, a measurement value measured by a sensor or the like installed in the manufacturing device, or a value obtained based on a calculation formula (a result of calculation) by using such a measurement value. For example, when a temperature sensor or a pressure sensor is used, measurement values measured by the sensors are also observation values. Moreover, for example, a "total amount of a raw material fed from start until a current time point", and a "total amount of all raw materials fed from start until a current time point" are also observation values. Note that a plurality of types of observation values may be used in prediction of the performance value and calculation of the target timing, and the number of observation values used is not limited. A plurality of different types of observation values acquired at the same time may be used, and some of types of observation values listed above may be used in combination.

Embodiment 1

A manufacturing device 1A according to an embodiment 1 is described by using FIGS. 1 to 7B. FIG. 1 is an example of the manufacturing device 1A used in manufacturing of an elastomer. The manufacturing device 1A shown in FIG. 1 includes: a prediction device 10A that predicts, by using a soft sensor, a Mooney viscosity that is a performance value specifying performance of an elastomer in a polymerization tank 3, in manufacturing of the elastomer that is manufactured by feeing raw materials into the polymerization tank 3; and a calculation device 20A that obtains, by using a soft sensor, a target timing in the manufacturing of the elastomer in the polymerization tank 3. Moreover, the manufacturing device 1A includes an operation unit 30 that performs a specific operation for terminating the current manufacturing by using the target timing obtained by the calculation device 20A.

The raw materials fed into the manufacturing device 1A include a monomer, an initiator, a chain transfer agent, and the like. Moreover, of the raw materials, some are fed initially, some are fed intermittently, some are fed continuously, and so forth, and the manufacturing device 1A according to the embodiment 1 is described by using a raw material that is fed intermittently or a raw material that is fed continuously, as an example.

Specifically, as shown in FIG. 1, the prediction device 10A predicts, from an "observation value", a "Mooney viscosity" that is a performance value of the elastomer at a predetermined timing in manufacturing, by using a Mooney viscosity prediction model M1 that is a first soft sensor. The calculation device 20A calculates a "target timing" in the manufacturing of the elastomer from the "Mooney viscosity" at the predetermined timing, by using a target timing calculation model M2 that is a second soft sensor. The manufacturing device 1A can finish feeding the material into the polymerization tank 3 by using the obtained target timing, and thus can terminate the manufacturing of the elastomer. For example, after the target timing is reached, the manufacturing device 1A can put the elastomer into an extractable state or the like, by finishing stirring or finishing adjusting temperature in the polymerization tank 3.

The manufacturing device 1A includes the polymerization tank 3 used for elastomer polymerization, and can output a control signal for controlling a stirrer 31 and receive a result of the control (for example, the number of rotations of the stirrer and the amount of electric current used for the rotations). Moreover, storage tanks 41, 42 that store the raw material are connected to the manufacturing device 1A, and the manufacturing device 1A can output a control signal for controlling feeding of the raw material. For example, the manufacturing device 1A can control a timing of feeding from the storage tanks 41, 42 to the polymerization tank 3, by using, as an observation value, a pressure value in the polymerization tank 3 measured by the pressure sensor 33.

In the following description, as an example, the manufacturing device 1A uses the Mooney viscosity prediction model M1 that is a trained model and the target timing calculation model M2 that is a trained model, for the first soft sensor and the second soft sensor, respectively, which, however, are not limited to the above-mentioned models. The first soft sensor may be a function that simply receives a required "observation value" as an input and predicts a "Mooney viscosity" of the elastomer at a predetermined timing. The second soft sensor may also be a function that simply receives the "Mooney viscosity" of the elastomer at the predetermined timing and a target "performance value" of the elastomer being manufactured as inputs and calculates a "target timing".

<Prediction Device>

Figure 2:
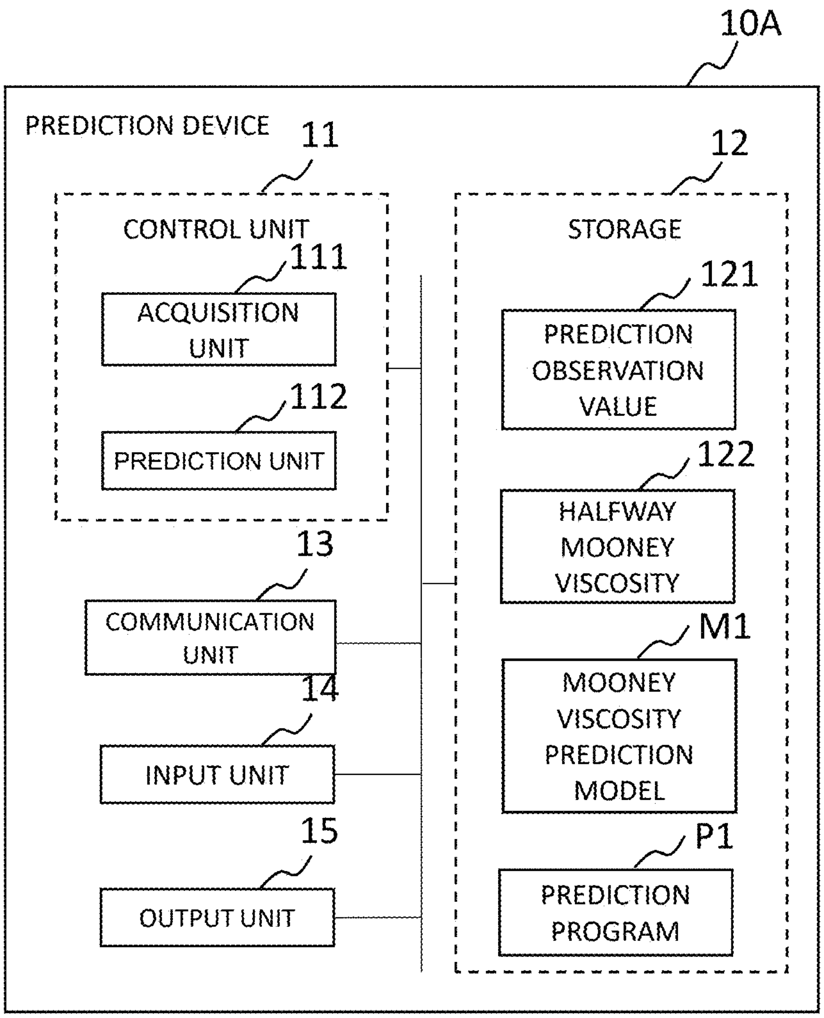
FIG. 2 is a block diagram showing a configuration of a prediction device in the embodiment 1.

As shown in FIG. 2, the prediction device 10A is an information processing device including a control unit 11, a storage 12, and a communication unit 13. The control unit 11 is a controller that controls the entire prediction device 10A. For example, the control unit 11 implements processing as an acquisition unit 111 and a prediction unit 112 by reading and executing a prediction program P1 stored in the storage 12. The control unit 11 is not limited to a unit that implements a predetermined function through cooperation between hardware and software, but may be a hardware circuit designed exclusively to implement the predetermined function. In other words, the control unit 11 can be implemented by using any of various processors such as CPU, MPU, GPU, FPGA, DSP, and ASIC.

The storage 12 is a recording medium storing various information. For example, the storage 12 is implemented by using a RAM, a ROM, a flash memory, an SSD (Solid State Drive), a hard disk, or any other storage device, or by combining any of such devices as appropriate. In addition to the prediction program P1 to be executed by the control unit 11, various data and the like to be used for learning and prediction are stored in the storage 12. For example, the storage 12 stores a prediction observation value 121, a halfway Mooney viscosity 122, the Mooney viscosity prediction model M1, and the prediction program P1. Note that the Mooney viscosity prediction model M1 may be included in the prediction program P1.

The communication unit 13 is an interface circuit (module) for enabling data communication with an external device (not shown).

The prediction device 10A can include an input unit 14 and an output unit 15. The input unit 14 is input devices, such as an operation button, a mouse, or a keyboard, used for input of an operation signal and data. The output unit 15 is output devices, such as a display, used for output of a result of processing and data, and other purposes.

The acquisition unit 111 acquires, as the prediction observation value 121, an observation value observed as a value related to manufacturing of the elastomer in current manufacturing. The acquisition unit 111 stores the prediction observation value 121 in the storage 12.

At the time, the acquisition unit 111 may acquire the observation value along with time information related to the current manufacturing, and may use a set of the time information and the observation value for the prediction observation value. The time information is, typically, elapsed time since start of the current manufacturing. Note that the time information may be other time information than the elapsed time. In other words, instead of the elapsed time, time information at which the manufacturing is started and time information at which each observation value is observed can be used for elapsed time since start of the manufacturing.

The prediction unit 112 predicts a Mooney viscosity of the elastomer being currently manufactured at a predetermined timing, from the prediction observation value acquired by the acquisition unit 111, by using a relation between an observation value acquired in past manufacturing of the same type of elastomer as the elastomer being currently manufactured and a Mooney viscosity of the elastomer at the predetermined timing in the past manufacturing. The "predetermined timing" is a timing after the raw material is fed and before the manufacturing is finished, and is, for example, a timing at which the fed amount of a predetermined raw material becomes a predetermined value, a timing at which a predetermined time period (for example, three hours) passes after start of the manufacturing, or the like. Note that in the following description, a "Mooney viscosity at the predetermined timing" is referred to as "halfway Mooney viscosity" as necessary.

The prediction unit 112 stores the predicted halfway Mooney viscosity 122 in the storage 12. Alternatively, the prediction unit 112 may output the halfway Mooney viscosity 122 to the calculation device 20A.

Here, the prediction unit 112 can use the Mooney viscosity prediction model M1, which is a trained model that has been trained through machine learning, in prediction of the halfway Mooney viscosity 122. The Mooney viscosity prediction model M1 has learned a relation between a training observation value, which is an observation value acquired in past manufacturing of the same type of elastomer as the elastomer being manufactured, and a halfway Mooney viscosity in the past manufacturing. Accordingly, the Mooney viscosity prediction model M1 can predict the halfway Mooney viscosity of the elastomer being manufactured, by receiving, as an input, the prediction observation value acquired by the acquisition unit 111. The machine learning will be described later by using FIG. 5A.

For example, when the Mooney viscosity prediction model M1 is a model using multiple regression analysis, the prediction-target "halfway Mooney viscosity" is an "objective variable" of the regression analysis, and the "observation value" is an "explanatory variable" of the regression analysis. The prediction observation value 121 that is input data of the Mooney viscosity prediction model M1 may be one observation value, or a combination of a plurality of observation values, selected, based on a genetic algorithm, from a plurality of types of observation values acquired in past manufacturing. Accordingly, the prediction observation value 121 selected based on the genetic algorithm is an observation value suitable for prediction of a Mooney viscosity. Specifically, when the Mooney viscosity prediction model M1 is built by using a selected observation value, the observation value is selected by using the genetic algorithm such that prediction performance of the Mooney viscosity prediction model M1 becomes higher.

For example, the prediction observation value 121 includes at least any of a "stirring electric current value" of the stirrer 31 that stirs a reaction mixture including the raw material in the polymerization tank 3, a "stirring electric power value", a "pressure value" in the polymerization tank 3, a "fed amount" of any of raw materials from start of the manufacturing until a current time point, and a "fed amount" of all raw materials from start of the manufacturing until a current time point. In other words, the prediction observation value 121 may be a value of one type, or a combination of values of multiple types, selected from among a plurality of the above-mentioned types.

Note that the prediction observation value 121 may be a measurement value actually measured by any of the sensors 32, 33 and flowmeters 43, 44, or a value calculated by using the measurement value. In such a case, for example, the acquisition unit 111 obtains the prediction observation value 121 by using the acquired measurement value, based on a predetermined calculation formula, and stores the prediction observation value 121 in the storage 12.

When the prediction observation value 121 includes the elapsed time along with the observation value, the prediction unit 112 predicts the halfway Mooney viscosity of the elastomer being manufactured in the current manufacturing, by using a relation between a training observation value as a set of the observation value in the past manufacturing and the elapsed time since start of the past manufacturing, and the halfway Mooney viscosity in the past manufacturing.

The halfway Mooney viscosity 122 is thus predicted by the prediction device 10A, whereby the Mooney viscosity of the elastomer being manufactured can be found, without a complicated process, such as sampling from the polymerization tank 3 and measuring the elastomer during the manufacturing. Since termination of the manufacturing of the elastomer can be determined by using the halfway Mooney viscosity, the number of manufacturing process steps can be reduced.

<Calculation Device>

Figure 3:
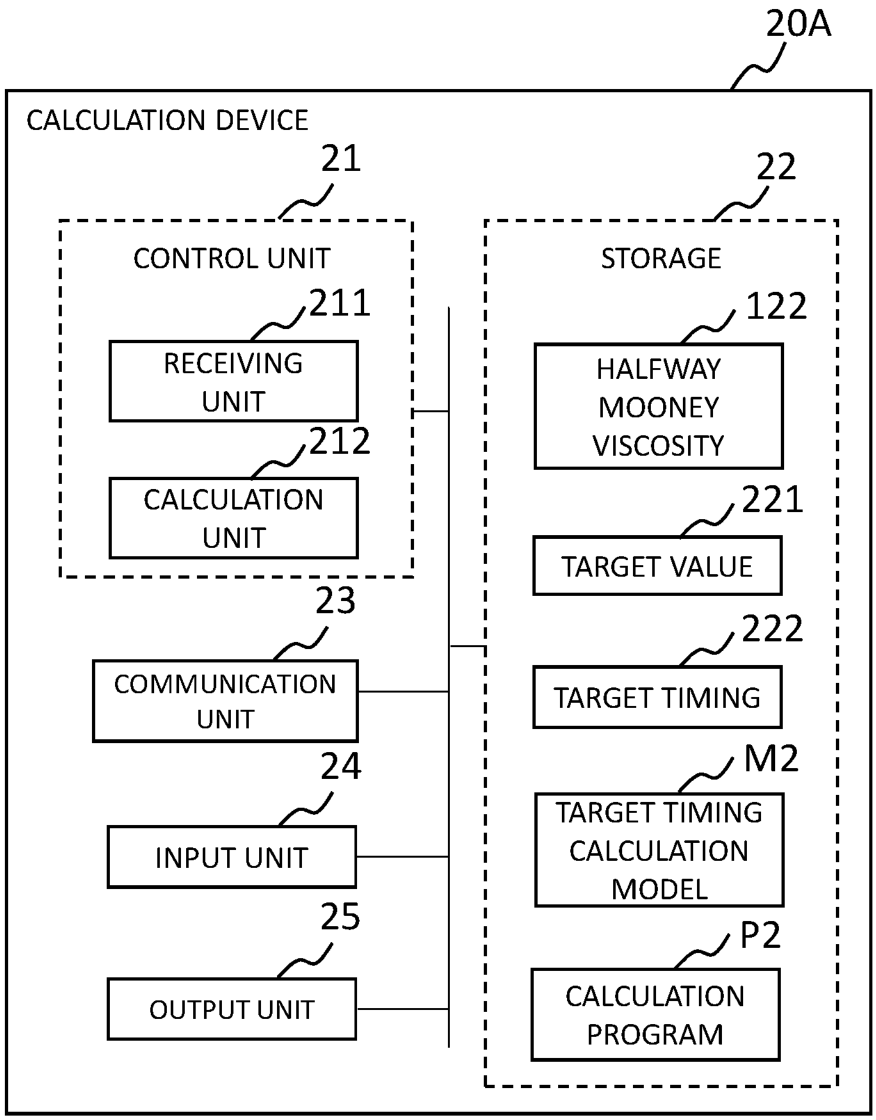
FIG. 3 is a block diagram showing a configuration of a calculation device in the embodiment 1.

As shown in FIG. 3, the calculation device 20A is an information processing device including a control unit 21, a storage 22, and a communication unit 23. Moreover, the calculation device 20A can include an input unit 24 and an output unit 25. For example, the control unit 21 implements processing as a receiving unit 211 and a calculation unit 212, by reading and executing a calculation program P2 stored in the storage 22. The storage 22 stores, for example, the halfway Mooney viscosity 122, a target value 221, a target timing 222, the target timing calculation model M2, and the calculation program P2. Note that the target timing calculation model M2 may be included in the calculation program P2.

The receiving unit 211 receives a performance value (halfway Mooney viscosity) of the elastomer at a predetermined timing, and a target Mooney viscosity of the elastomer in current manufacturing. In the following description, the "target Mooney viscosity" is referred to as "target value" as necessary. For example, the halfway Mooney viscosity 122 received by the receiving unit 211 may be the halfway Mooney viscosity predicted by the prediction device 10A. The receiving unit 211 stores the received halfway Mooney viscosity 122 and the received target value 221 in the storage 22.

For example, when an elastomer with the same performance is manufactured multiple times, the calculation device 20A does not need to receive a new target value each time, but may read and use the target value 221 received in the past and stored in the storage 22.

The calculation unit 212 obtains a target timing used to determine termination of the current manufacturing of the elastomer, by using a relation among a halfway Mooney viscosity in past manufacturing of the same type of elastomer as the elastomer being manufactured, a final Mooney viscosity of the elastomer acquired in the past manufacturing, and a target timing in the manufacturing of the elastomer, and by using the target value and the halfway Mooney viscosity received by the receiving unit 211. The calculation unit 212 outputs the obtained target timing to the operation unit 30. Note that all of the halfway Mooney viscosity, the final Mooney viscosity, and the target timing in the past manufacturing are actually measured values.

Here, the calculation unit 212 can use the target timing calculation model M2, which is a trained model that has been trained through machine learning, in calculation of the target timing 222. The target timing calculation model M2 has learned, through machine learning, a relation among a past halfway Mooney viscosity of the same type of elastomer as the elastomer being manufactured, a final Mooney viscosity, and a target timing. Accordingly, by using the target value 221 and the halfway Mooney viscosity 122 received by the receiving unit 211, the target timing calculation model M2 can obtain the target timing used to determine termination of the current manufacturing of the elastomer, in order to allow performance of the elastomer being currently manufactured to be the target value. The machine learning will be described later by using FIG. 7A.

The target timing 222 is thus obtained by the calculation device 20A, whereby the manufacturing process can be terminated when the Mooney viscosity of the elastomer is in a target state. Accordingly, by using the target timing 222 obtained as a result of the calculation, variation in the Mooney viscosity of the elastomer being manufactured can be reduced, compared to a conventional simple soft sensor. Note that even if the manufacturing is terminated based on the target timing obtained by the calculation device 20A by using the target value, the Mooney viscosity (final Mooney viscosity) of the acquired elastomer does not necessarily coincide with the target value, but comes within a desired range from the target value.

The above description uses an example in which the receiving unit 211 receives the halfway Mooney viscosity predicted by the prediction device 10A. However, when the elastomer being manufactured can be sampled from the polymerization tank 3 and actually measured, the receiving unit 211 may receive an actually measured halfway Mooney viscosity. In particular, when the prediction device 10A cannot accurately predict a halfway Mooney viscosity due to impossibility of acquiring an accurate observation value as a result of an abnormality occurring in equipment or the like that acquires an observation value, it is effective to stop using the prediction device 10A, and use a halfway Mooney viscosity of the elastomer being manufactured that is sampled from the polymerization tank 3.

Although the prediction device 10A, the calculation device 20A, and the operation unit 30 are shown as separate entities in the example in FIG. 1, two or more of the entities may be configured by using a single information processing device. For example, all the entities may be configured by using a single information processing device, or the prediction device 10A and the calculation device 20A, or the calculation device 20A and the operation unit 30, may be configured by using a single information processing device.

<Manufacturing Method>

Figure 4:
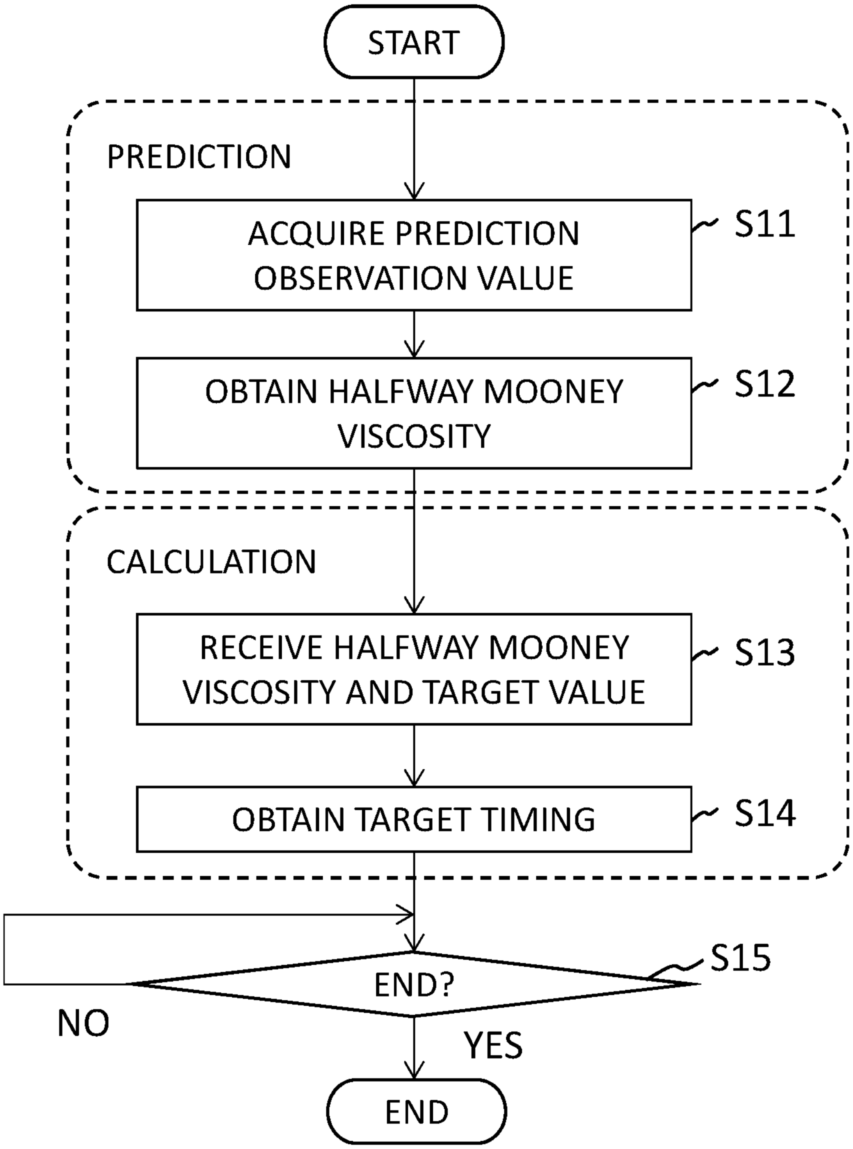
FIG. 4 is a flowchart for describing processing in the manufacturing device in the embodiment 1.

Elastomer manufacturing processing in the manufacturing device 1A is described by using a flowchart of FIG. 4. When the manufacturing device 1A starts manufacturing an elastomer, the acquisition unit 111 of the prediction device 10A acquires a prediction observation value 121 (S11). Note that the acquisition unit 111 may acquire the prediction observation value 121 through calculation by using a value acquired from an external sensor or device.

The prediction unit 112 obtains a halfway Mooney viscosity 122 of the elastomer being manufactured, by using the prediction observation value 121 acquired in step S11 (S12).

Thus, the manufacturing device 1A can acquire the halfway Mooney viscosity, without actual measurement through a complicated process.

The receiving unit 211 of the calculation device 20A receives the halfway Mooney viscosity 122 obtained in step S12 and a target value 221 of the elastomer being manufactured (S13).

The calculation unit 212 obtains a target timing 222 used to determine termination of the manufacturing of the elastomer being manufactured, by using the halfway Mooney viscosity 122 and the target value 221 received in step S13 (S14).

Thus, by using the target timing 222 obtained in step S14, the manufacturing device 1A continues manufacturing of the elastomer until a condition for termination is met, and terminates the manufacturing of the elastomer when the condition is met (S15).

Thus, the manufacturing device 1A can reduce the number of manufacturing process steps because a sample inspection is not needed and a step of the manually performed inspection can therefore be eliminated.

Note that the processing in steps S11 and S12 is performed by the prediction device 10A, and the processing in steps S13 and S14 is performed by the calculation device 20B. If it is possible for the manufacturing device 1A to actually measure a halfway Mooney viscosity, in step S13, the receiving unit 211 may receive a halfway Mooney viscosity actually measured by sampling the elastomer being manufactured, and in step S14, the calculation unit 212 may obtain a target timing by using the actually measured halfway Mooney viscosity. In such a case, the target timing at which the target value is achieved can be obtained from a soft sensor acquired based on a rule of past experiences, by using the sampled halfway Mooney viscosity.

Here, the manufacturing device 1A may be implemented by a single computer, or may be implemented by a combination of a plurality of computers connected through a network. For example, the prediction device 10A shown in FIG. 2 and the calculation device 20A shown in FIG. 3 do not need to be different computers, but may be implemented by using the same computer. In such a case, the control units 11, 21 are the same unit, as well as the storages 12, 22, the communication units 13, 23, the input units 14, 24, and the output units 15, 25. Moreover, for example, all or part of the data stored in the storage 12 may be stored in an external recording medium connected through a network, and the prediction device 10A may be configured to use the data stored in the external recording medium.

<Machine Learning>

Figure 5A:
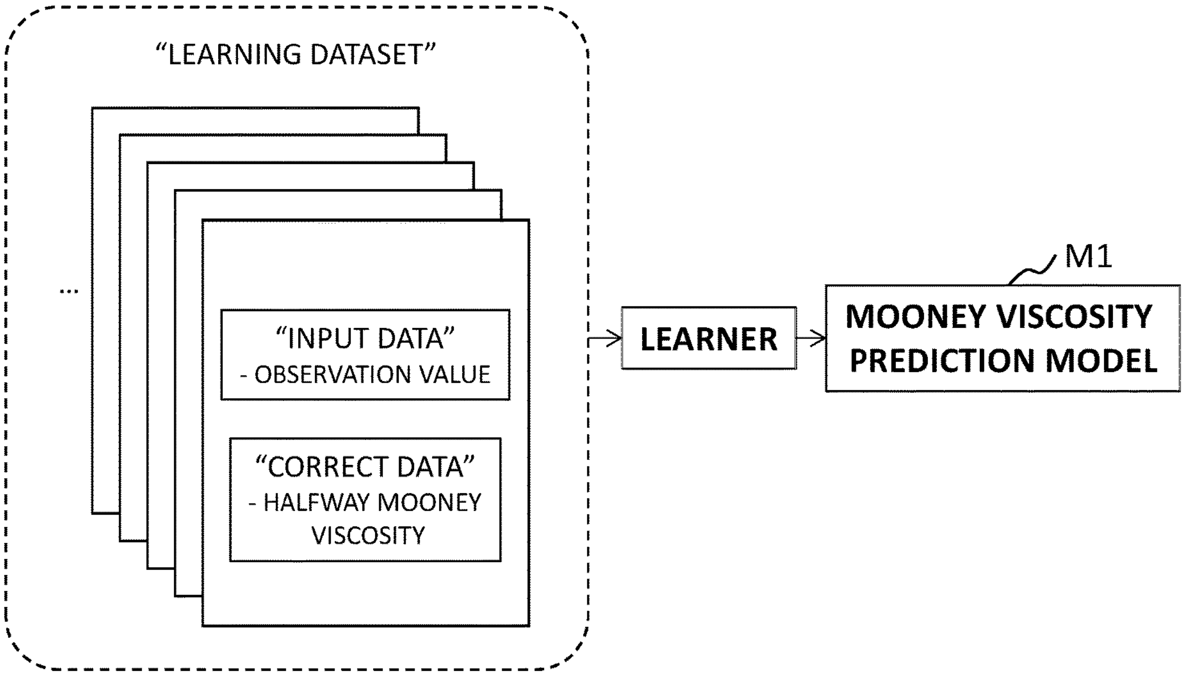
FIG. 5A is a schematic diagram for describing learning by a Mooney viscosity prediction model used by the prediction device in the embodiment 1.
Figure 5B:
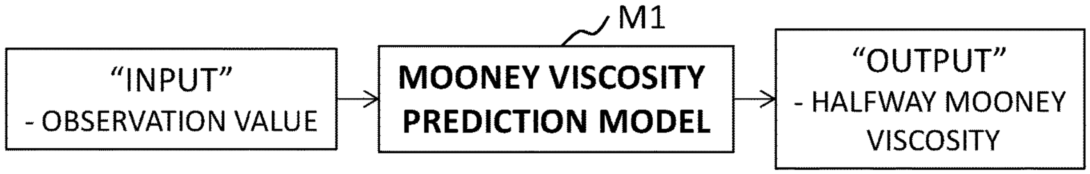
FIG. 5B is a schematic diagram for describing input to and output from the Mooney viscosity prediction model used by the prediction device in the embodiment 1.
Figure 7A:
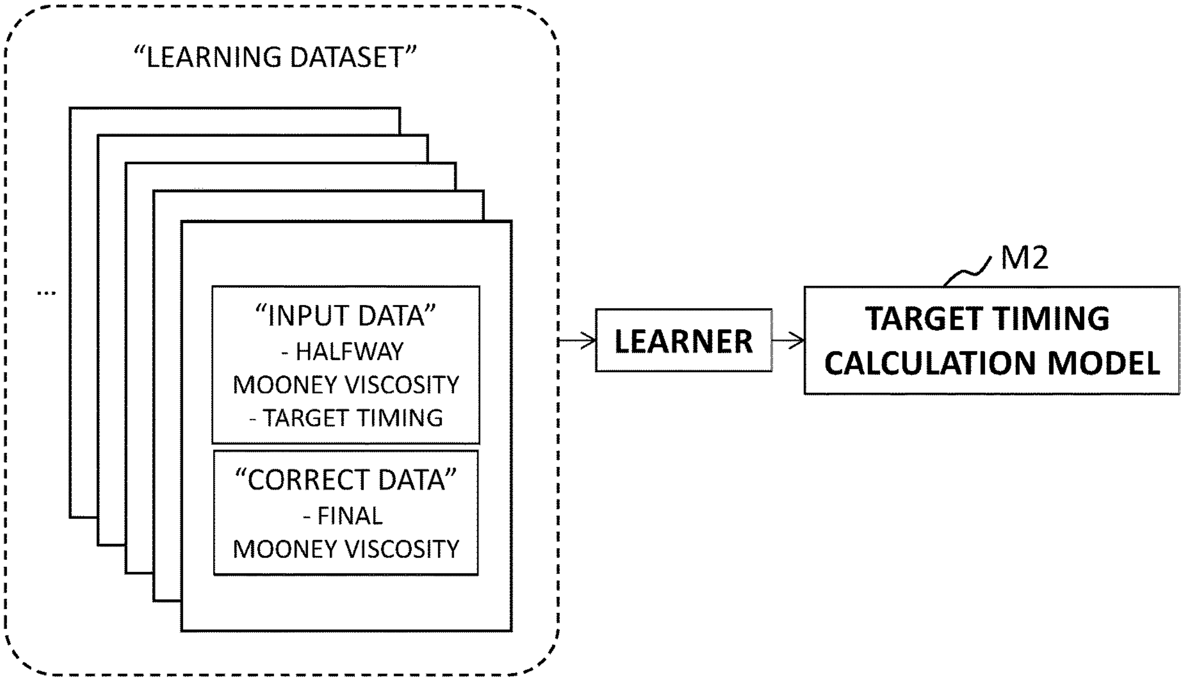
FIG. 7A is a schematic diagram for describing learning by a target timing calculation model used by the calculation device in the embodiment 1.
Figure 7B:
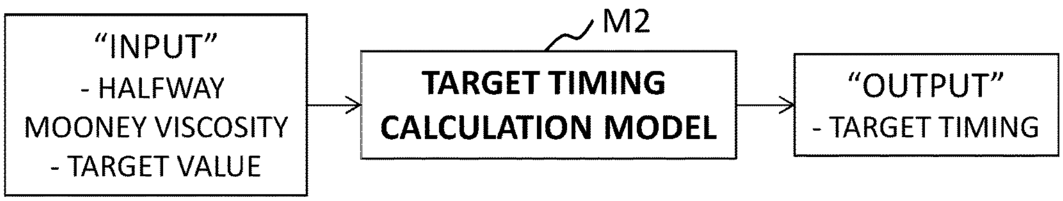
FIG. 7B is a schematic diagram for describing input to and output from the target timing calculation model used by the calculation device in the embodiment 1.

An outline of creation and use of the Mooney viscosity prediction model M1 using machine learning is illustrated by using FIGS. 5A and 5B, and an outline of creation and use of the target timing calculation model M2 using machine learning is illustrated by using FIGS. 7A and 7B. The "machine learning" is a scheme for creating a "model" that learns a feature included in input data and infers a result corresponding to new input data. Specifically, the machine learning is performed by a "learner". The thus created model is referred to as "trained model".

As shown in FIG. 5A, a plurality of pairs of input data and correct data acquired in past manufacturing of the elastomer are inputted into the "learner". Specifically, when the Mooney viscosity prediction model M1 is created, an "observation value" acquired in past manufacturing of the elastomer is used for input data, and a "halfway Mooney viscosity" actually measured in the past manufacturing of the elastomer is used for correct data. Thus, the learner learns a relation between such observation values and halfway Mooney viscosities, which is a learning dataset relation, and creates the Mooney viscosity prediction model M1 that is a trained model indicating the relation between the observation values and the halfway Mooney viscosities with parameters. By using the created Mooney viscosity prediction model M1, a "halfway Mooney viscosity" that is a desired output can be obtained for an "observation value" that is a new input, as shown in FIG. 5B. Accordingly, an output obtained by the Mooney viscosity prediction model M1 is a "halfway Mooney viscosity" as a prediction value, not an actually measured value.

Figure 6:
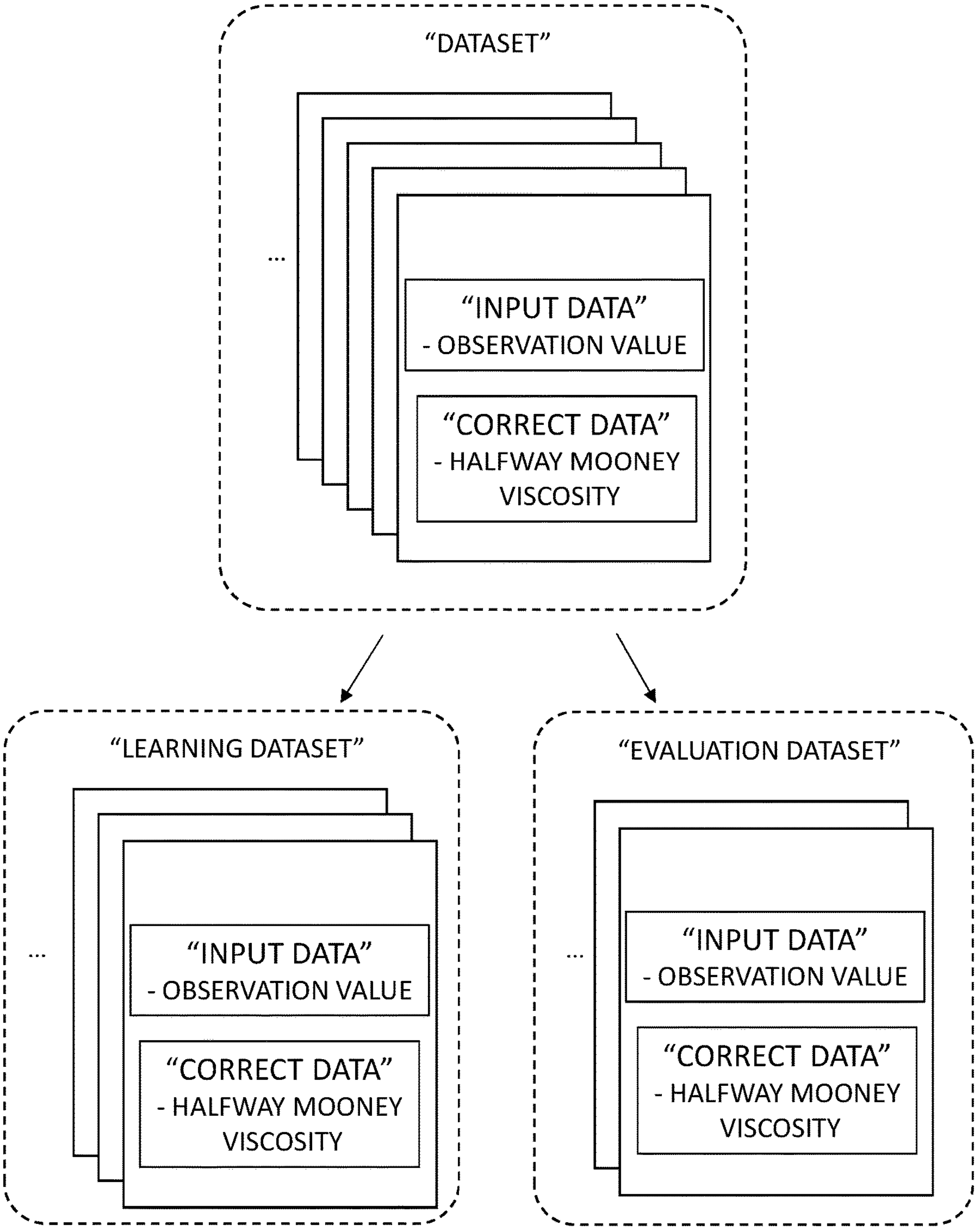
FIG. 6 is a schematic diagram for describing teaching data for the Mooney viscosity prediction model used by the prediction device in the embodiment 1.

More specifically, in the machine learning, when the trained model is created, a "dataset" is used that is formed of a plurality of pairs of "input data", which is an observation value acquired in past manufacturing of the elastomer, and "correct data", which is a halfway Mooney viscosity of the elastomer acquired in the corresponding manufacturing, as shown in FIG. 6. At the time, part of the "dataset" acquired through the past operation is used for a learning dataset for "learning", and the rest is used for an evaluation dataset for "evaluation" to check the learning. The learning dataset is also referred to as a training dataset. The evaluation dataset is also referred to as, for example, a test dataset.

Note that when the "dataset" is divided into the "learning dataset" and the "evaluation dataset", it is preferable to use chronologically older data for the "learning dataset" and newer data for the "evaluation dataset". For example, observation values acquired in manufacturing by the manufacturing device 1A can vary over time. For example, regarding observation values affected by aging of equipment, a plurality of observation values acquired at close times may be more similar to each other, than to an observation value acquired at a distant time. Accordingly, newer data tends to be similar to data to be acquired in future manufacturing. In such a case, by using a newer observation value in evaluation, it is more likely that the prediction model can be evaluated with the observation value that is more similar to an observation value in actual future manufacturing by the manufacturing device 1A. Accordingly, of the data acquired in the past manufacturing, for example, a predetermined proportion of older data is used for the learning dataset, and the rest newer data is used for the evaluation dataset, whereby the Mooney viscosity prediction model M1 can be evaluated with the data that is similar to data to be acquired in future manufacturing.

As shown in FIG. 7A, when the target timing calculation model M2 is created, a "halfway Mooney viscosity" and a "target timing" that are actually measured are used for input data, and an actually measured "final Mooney viscosity" is used for correct data. Thus, the learner learns a relation among such halfway Mooney viscosities, target timings, and final Mooney viscosities, which is a learning dataset relation, and creates the target timing calculation model M2 that is a trained model indicating the learning dataset relation with parameters. As described above, a final Mooney viscosity is a Mooney viscosity actually measured for the elastomer acquired in past manufacturing. Accordingly, by using the learning dataset shown in FIG. 7A, a relation about what performance the manufactured elastomer has in a case of each halfway Mooney viscosity and each target timing can be learned. As shown in FIG. 7B, the thus created target timing calculation model M2 receives a "halfway Mooney viscosity" and a "target value" as inputs, and can obtain a "target timing" at which the final Mooney viscosity becomes the target value. The "halfway Mooney viscosity" as an input of the target timing calculation model M2 may be an actually measured value, or a highly accurate prediction value. Accordingly, a halfway Mooney viscosity obtained by the Mooney viscosity prediction model M1 may be used for an input of the target timing calculation model M2, or an input may be an actually measured halfway Mooney viscosity.

As for data used to create the target timing calculation model M2, a description of which using a drawing is omitted, it is also preferable to select a learning dataset from older data, and to select a test dataset from newer data, as described by using FIG. 6.

Machine learning includes supervised learning, unsupervised learning, reinforcement learning, and the like, and the examples described with FIGS. 5A and 7A are supervised learning. The learner can use, for example, the above-described multiple regression analysis or the like for the machine learning. The learner may use another regression than the multiple regression analysis (for example, PCR (Principal Component Regression), PLS (Partial Least Squares), SVR (Support Vector Regression), DT (Decision Tree), RF (Random Forest), GPR (Gaussian Process Regression), NN (Neural Network), Model Tree, or the like). TD (Time Difference), JIT (Just In Time), or MW (Moving Window) may be prefixed to each of the above-mentioned algorithms. The learner may use LWPLS (Locally Weighted Partial Least Squares). The learner may use any of the above-mentioned schemes in combination.

Embodiment 2

Figure 8:
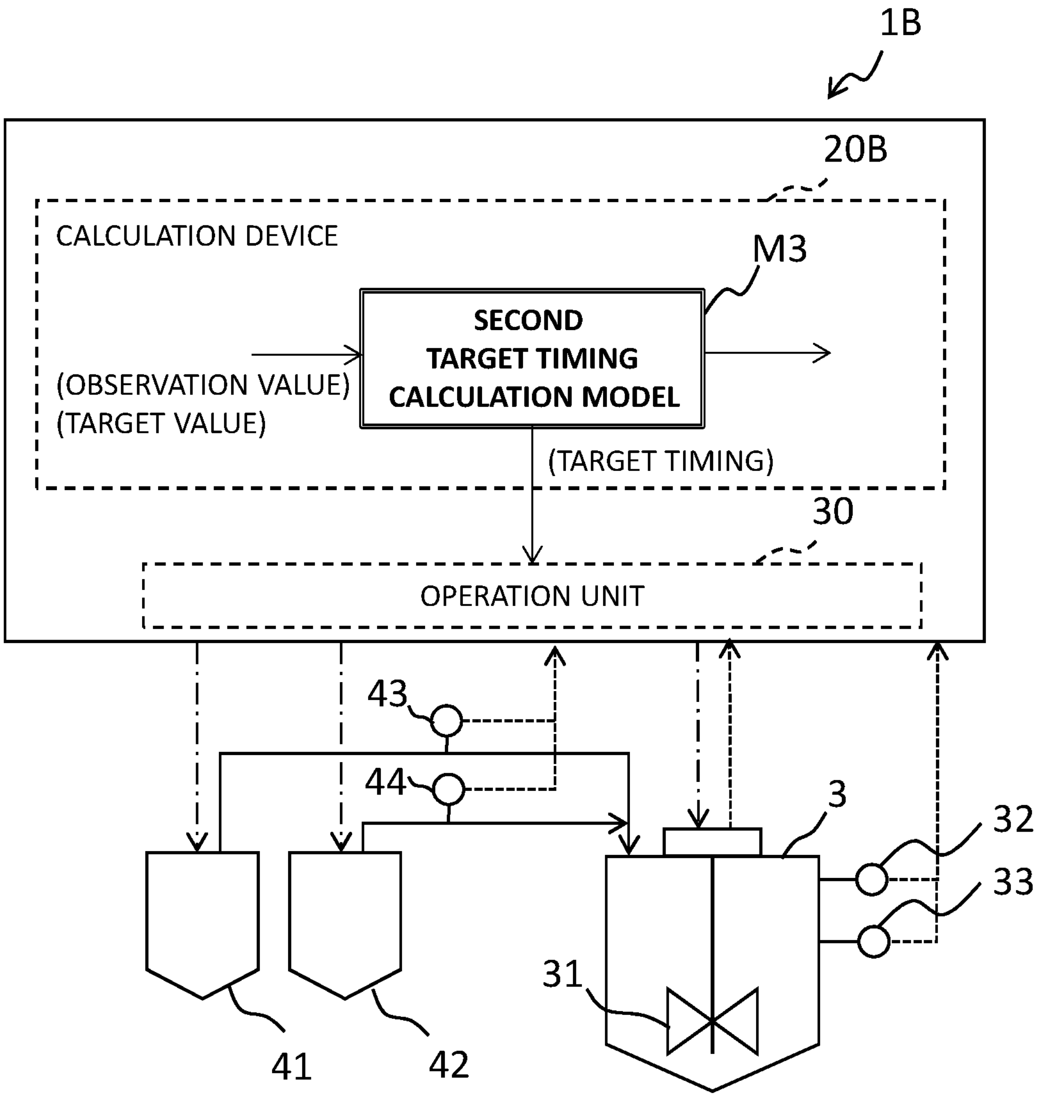
FIG. 8 is a schematic diagram showing a configuration of a manufacturing device in an embodiment 2.

A manufacturing device 1B according to an embodiment 2 is described by using FIGS. 8 to 11B. FIG. 8 is an example of the manufacturing device 1B used in manufacturing of an elastomer. The manufacturing device 1B shown in FIG. 8 includes a calculation device 20B that obtains, in manufacturing of an elastomer that is manufactured by feeding raw materials into a polymerization tank 3, a target timing in the manufacturing of the elastomer by using a soft sensor. The manufacturing device 1B includes an operation unit 30 that performs a specific operation for terminating the current manufacturing, by using the target timing obtained by the calculation device 20B. Note that in the manufacturing device 1B according to the embodiment 2, a description of the same components as those of the manufacturing device 1A described above is omitted by using the same drawings. In the description of the manufacturing device 1B, it is also assumed that a raw material is fed intermittently or fed continuously.

Specifically, as shown in FIG. 8, the calculation device 20B obtains a "target timing" in manufacturing of the elastomer from an "observation value", by using a second target timing calculation model M3 that is a third soft sensor. The manufacturing device 1B can finish feeding the material into the polymerization tank 3 by using the obtained target timing, and thus can terminate the manufacturing of the elastomer. Specifically, after the target timing is reached, the manufacturing device 1B can put the elastomer into an extractable state, by finishing stirring or finishing adjusting temperature in the polymerization tank 3.

<Calculation Device>

Figure 9:
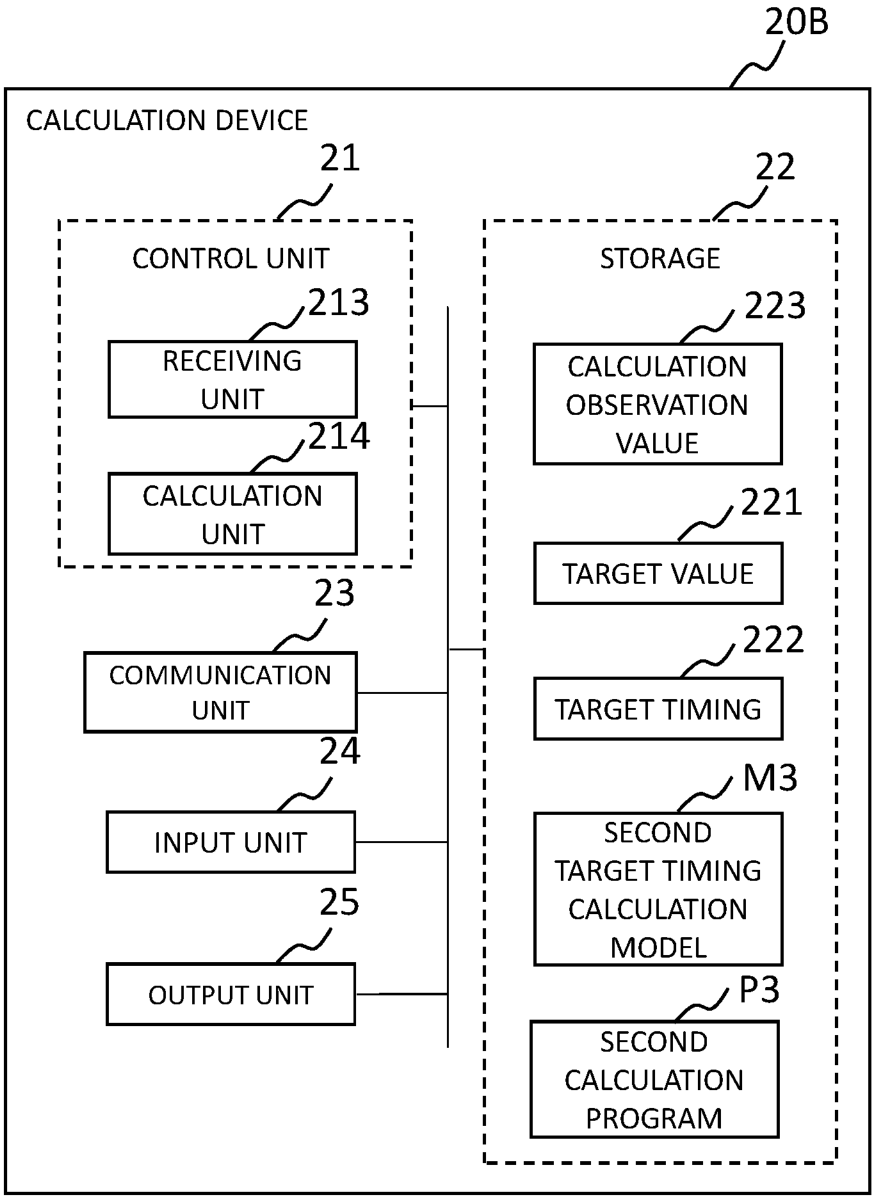
FIG. 9 is a block diagram showing a configuration of a calculation device in the embodiment 2.

As shown in FIG. 9, the calculation device 20B is an information processing device including a control unit 21, a storage 22, and a communication unit 23. Moreover, the calculation device 20B can include an input unit 24 and an output unit 25. For example, the control unit 21 implements processing as a receiving unit 213 and a calculation unit 214 by reading and executing a second calculation program P3 stored in the storage 22. The storage 22 stores, for example, a calculation observation value 223, a target value 221, a target timing 222, the second target timing calculation model M3, and the second calculation program P3. Note that the second target timing calculation model M3 may be included in the second calculation program P3.

The receiving unit 213 receives, as the calculation observation value 223, an observation value observed as a value related to manufacturing of the elastomer in current manufacturing. Note that the calculation observation value 223 may be identical to the prediction observation value 121 described above. The receiving unit 213 receives the target value 221 in the current manufacturing. The receiving unit 213 stores the received calculation observation value 223 and the received target value 221 in the storage 22.

The calculation unit 214 obtains a target timing in the current manufacturing, from the calculation observation value 223 and the target value 221 received by the receiving unit 213, by using a relation among an observation value acquired in past manufacturing of the same type of elastomer as the elastomer being manufactured, a final Mooney viscosity of the elastomer manufactured in the past manufacturing, and a target timing in the past manufacturing. Note that all of the observation value, the final Mooney viscosity, and the target timing in the past manufacturing are actually measured values.

Here, in calculation of the target timing, the calculation unit 214 can use the second target timing calculation model M3, which is a trained model that has been trained through machine learning. The second target timing calculation model M3 has learned, through machine learning, a relation among a training observation value that is an observation value acquired in past manufacturing of the same type of elastomer as the elastomer being manufactured, a final Mooney viscosity of the elastomer acquired in the past manufacturing, and a target timing in the past manufacturing. Accordingly, the second target timing calculation model M3 can obtain the target timing used to determine termination of the current manufacturing of the elastomer, by using the calculation observation value and the target value received by the receiving unit 213, in order to allow performance of the elastomer being currently manufactured to be the target value. The machine learning will be described later by using FIG. 11A.

Note that the calculation device 20B and the operation unit 30 are shown as separate entities in the example in FIG. 8, but may be configured by using a single information processing device.

The target timing 222 is thus obtained by the calculation device 20B, whereby manufacturing can be terminated when the Mooney viscosity of the elastomer is in a target state. Accordingly, by using the target timing 222 obtained as a result of the calculation, the number of process steps related to actual measurement can be reduced. Note that even if the manufacturing is terminated by using the target timing obtained by the calculation device 20B by using the target value, the Mooney viscosity (final Mooney viscosity) of the acquired elastomer does not necessarily coincide with the target value, but comes within a desired range from the target value. By using the second target timing calculation model M3, variation in elastomer quality can be reduced, compared to a conventional simple soft sensor.

<Manufacturing Processing>

Figure 10:
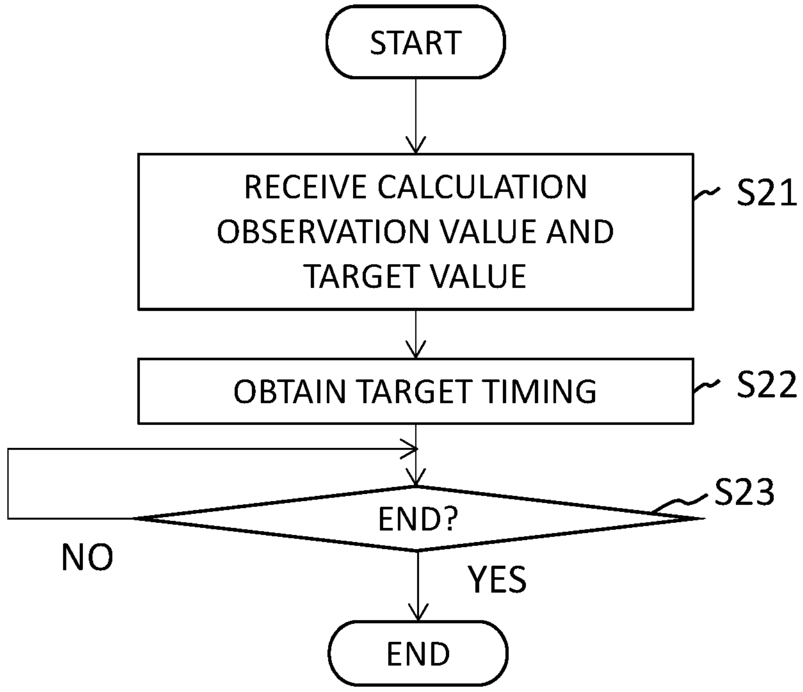
FIG. 10 is a flowchart for describing processing in the manufacturing device in the embodiment 2.

Elastomer manufacturing processing in the manufacturing device 1B is described by using a flowchart of FIG. 10. When the manufacturing device 1B starts manufacturing an elastomer, the receiving unit 213 of the calculation device 20B acquires a calculation observation value 223 and a target value 221 (S21). Note that the acquisition unit 111 may obtain the calculation observation value 223 through calculation by using a value received from an external sensor or device.

The calculation unit 214 obtains a target timing 222 used to determine termination of the manufacturing of the elastomer being manufactured, by using the calculation observation value 223 and the target value 221 received in step S21 (S22).

Thus, by using the calculation observation value 223 and the target timing 222 obtained in step S22, the manufacturing device 1B continues manufacturing of the elastomer until a condition for termination is met, and terminates the manufacturing of the elastomer when the condition is met (S23).

Thus, the manufacturing device 1B can reduce the number of process steps related to actual measurement, without needing a sample inspection, and can reduce variation in elastomer quality through an easy procedure.

<Machine Learning>

Figure 11A:
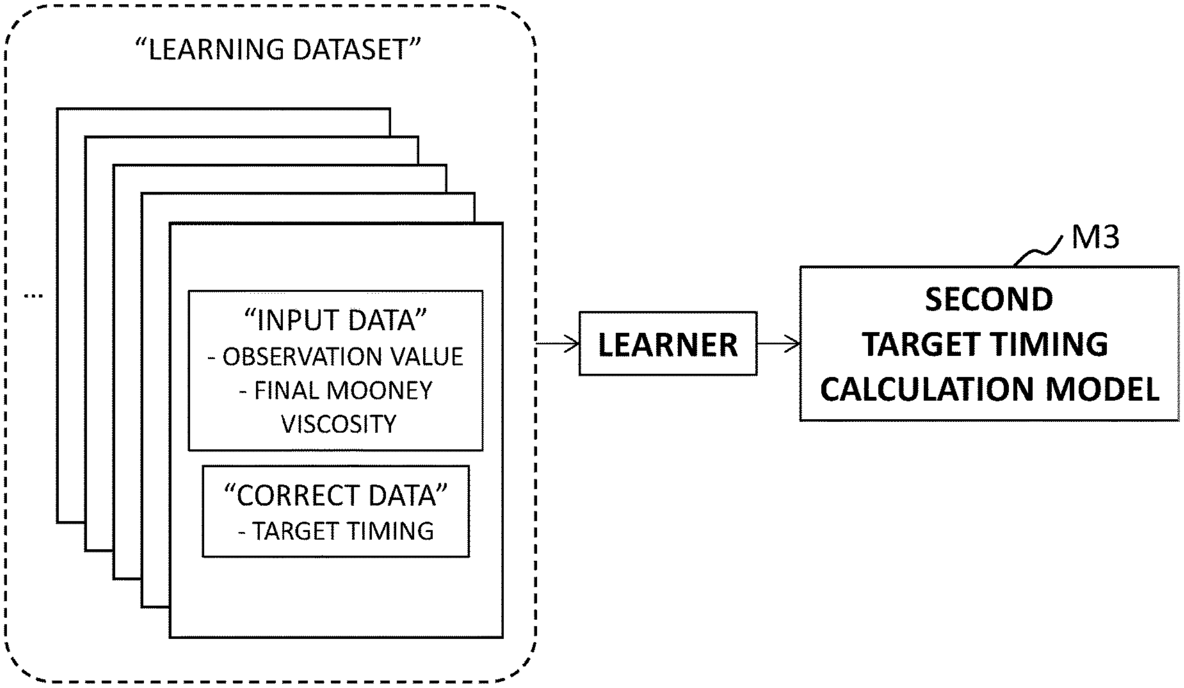
FIG. 11A is a schematic diagram for describing learning by a Mooney viscosity prediction model used by a prediction device in the embodiment 2.
Figure 11B:
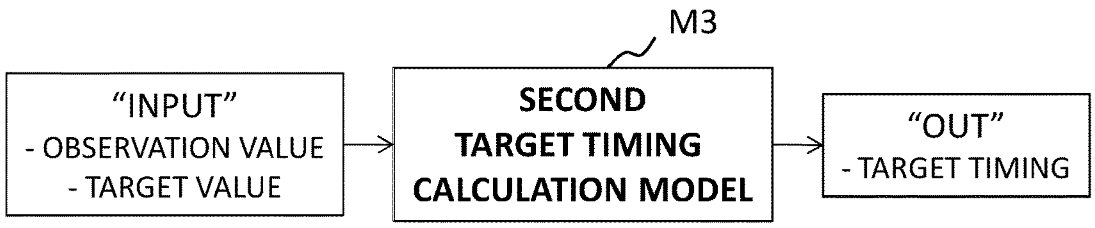
FIG. 11B is a schematic diagram for describing input to and output from the Mooney viscosity prediction model used by the prediction device in the embodiment 2.

An outline of creation and use of the second target timing calculation model M3 using machine learning is illustrated by using FIGS. 11A and 11B. As shown in FIG. 11A, when the second target timing calculation model M3 is created, an "observation value" acquired in past manufacturing of the elastomer and a "final Mooney viscosity" actually measured for the elastomer acquired in the past manufacturing are used for input data, and a "target timing" actually measured in the past manufacturing of the elastomer is used for correct data. A learner learns a relation among such observation values, final Mooney viscosities, and target timings, which is a learning dataset relation, and creates the second target timing calculation model M3 that is a trained model indicating the learning dataset relation with parameters. As described above, a final Mooney viscosity is a Mooney viscosity actually measured for the elastomer acquired in past manufacturing. Accordingly, by using the learning dataset shown in FIG. 11A, a relation about what target timing is set in a case of each observation value and each final Mooney viscosity can be indicated. As shown in FIG. 11B, the thus created second target timing calculation model M3 receives an "observation value" and a "target value" as inputs, and can obtain a "target timing" at which the final Mooney viscosity becomes the target value.

ADVANTAGEOUS EFFECTS AND SUPPLEMENTS

As described above, each embodiment is described as illustration of the technique disclosed in the present application. However, the technique of the present disclosure is not limited to the described embodiments, and can be applied to embodiments in which a change, a substitution, an addition, an omission, or the like is made as appropriate.

A prediction device, a calculation device, a manufacturing device, and a manufacturing method according to all claims of the present disclosure are implemented by cooperation or the like with hardware resources, such as a processor and a memory, and a program.

The present application claims priority based upon Japanese Patent Application No. 2020-115514, filed on Jul. 3, 2020 in Japan, the disclosure of which is incorporated herein in its entirety by reference.

INDUSTRIAL APPLICABILITY

The prediction device, the calculation device, the manufacturing device, and the manufacturing method of the present disclosure are useful for, for example, manufacturing of a polymer.

What is claimed is:

1. A prediction device that, in manufacturing of an elastomer, predicts a performance value indicating performance of the elastomer in a polymerization tank at a predetermined timing after a raw material is fed and before the manufacturing is terminated, comprising:

an acquisition unit configured to acquire, as a prediction observation value, an observation value observed, in current manufacturing of the elastomer, as a value related to the manufacturing of the elastomer; and a prediction unit configured to predict the performance value of the elastomer being currently manufactured at the predetermined timing, from the prediction observation value acquired by the acquisition unit, by using a relation between an observation value acquired in past manufacturing of the same type of elastomer as the elastomer, and a performance value of the elastomer at the predetermined timing in the past manufacturing, wherein the performance value is any of a Mooney viscosity, a molecular mass, a specific gravity, a hardness, an elongation, a minimum torque, a maximum torque, an induction time to start of curing, an optimal curing time, a tensile strength, a 100% tensile stress, a glass transition point, an initial pyrolysis temperature, and a compression set rate;

wherein the prediction unit is configured to predict the performance value of the elastomer being currently manufactured at the predetermined timing, from the prediction observation value acquired by the acquisition unit, by using a trained model that has learned, through machine learning, a relation between a training observation value acquired in past manufacturing of the same type of elastomer as the elastomer, and a performance value of the elastomer at the predetermined timing in the past manufacturing;

the acquisition unit is configured to acquire the observation value along with elapsed time since start of the current manufacturing, and uses a set of the elapsed time and the observation value for the prediction observation value;

the prediction unit is configured to predict the performance value of the elastomer being currently manufactured at the predetermined timing, by using a relation between a training observation value that is a set of the observation value in the past manufacturing and elapsed time since start of the past manufacturing, and the performance value at the predetermined timing in the past manufacturing;

wherein the observation value includes at least any of a stirring electric current value of a stirrer that stirs a reaction mixture including the raw material in the polymerization tank, a stirring electric power value, a pressure value in the polymerization tank, an amount of any of raw materials fed from start of manufacturing until a current time point, and an amount of all raw materials fed from start of manufacturing until a current time point; and the prediction device is configured to output a control signal to an operation unit to perform a specific operation for terminating the current manufacturing based on the predicted performance value at the predetermined timing.

2. The prediction device according to claim 1, wherein the prediction unit is configured to predict the performance value of the elastomer at the predetermined timing, by using the trained model that is trained by using at least one observation value or performance value suitable for prediction of the performance value, the at least one observation value or performance value being selected, based on a genetic algorithm, from a plurality of types of observation values acquired in the past manufacturing and performance values of the elastomer acquired in the past manufacturing.

3. The prediction device according to claim 1, wherein the predetermined timing is a timing at which a fed amount of a predetermined raw material of the elastomer being manufactured becomes a predetermined value, or a timing at which a predetermined time period passes after start of manufacturing.

* * * * *